United States Patent [19]

Krolikowski et al.

[11] Patent Number: 4,642,101
[45] Date of Patent: Feb. 10, 1987

[54] NON-TRAUMATIC BULBOUS CATHETER

[76] Inventors: F. John Krolikowski, 10 Sheehan Cir., Wellesley Hills, Mass. 02181; Albert Shahnarian, 144 Worcester Rd., Princeton, Mass. 01541

[21] Appl. No.: 734,509

[22] Filed: May 16, 1985

[51] Int. Cl.$^4$ ........................ A61M 5/00; A61M 25/02
[52] U.S. Cl. ..................................... 604/164; 604/174; 128/DIG. 26
[58] Field of Search .............................. 604/164–170, 604/280, 283, 174; 128/DIG. 26

[56] References Cited

U.S. PATENT DOCUMENTS

| | | | |
|---|---|---|---|
| 2,910,981 | 11/1959 | Wilson et al. | 604/114 |
| 3,176,690 | 4/1965 | H'Doubler | 604/174 |
| 3,884,220 | 5/1975 | Hartnett | 604/164 X |
| 4,230,110 | 10/1980 | Beroff | 604/174 |
| 4,388,076 | 6/1983 | Waters | 604/165 |

FOREIGN PATENT DOCUMENTS 1512435 2/1968 France .................................. 604/164

OTHER PUBLICATIONS

Gaertner–Surgery, Gyne & Obstetrics vol. 119, No. 3, pp. 599–600.

Primary Examiner—Dalton L. Truluck
Attorney, Agent, or Firm—Donald W. Meeker

[57] ABSTRACT

A smooth bulbous tip slips within a blood vessel after puncture by an inserted needle. Withdrawal of the needle leaves a blunt, non-lacerating conduit for intravenous fluid. A broad base prevents breakage of the cannula. Multiple break-away perforated tabs provide options for suturing the hub of the catheter to the skin of the patient.

4 Claims, 7 Drawing Figures

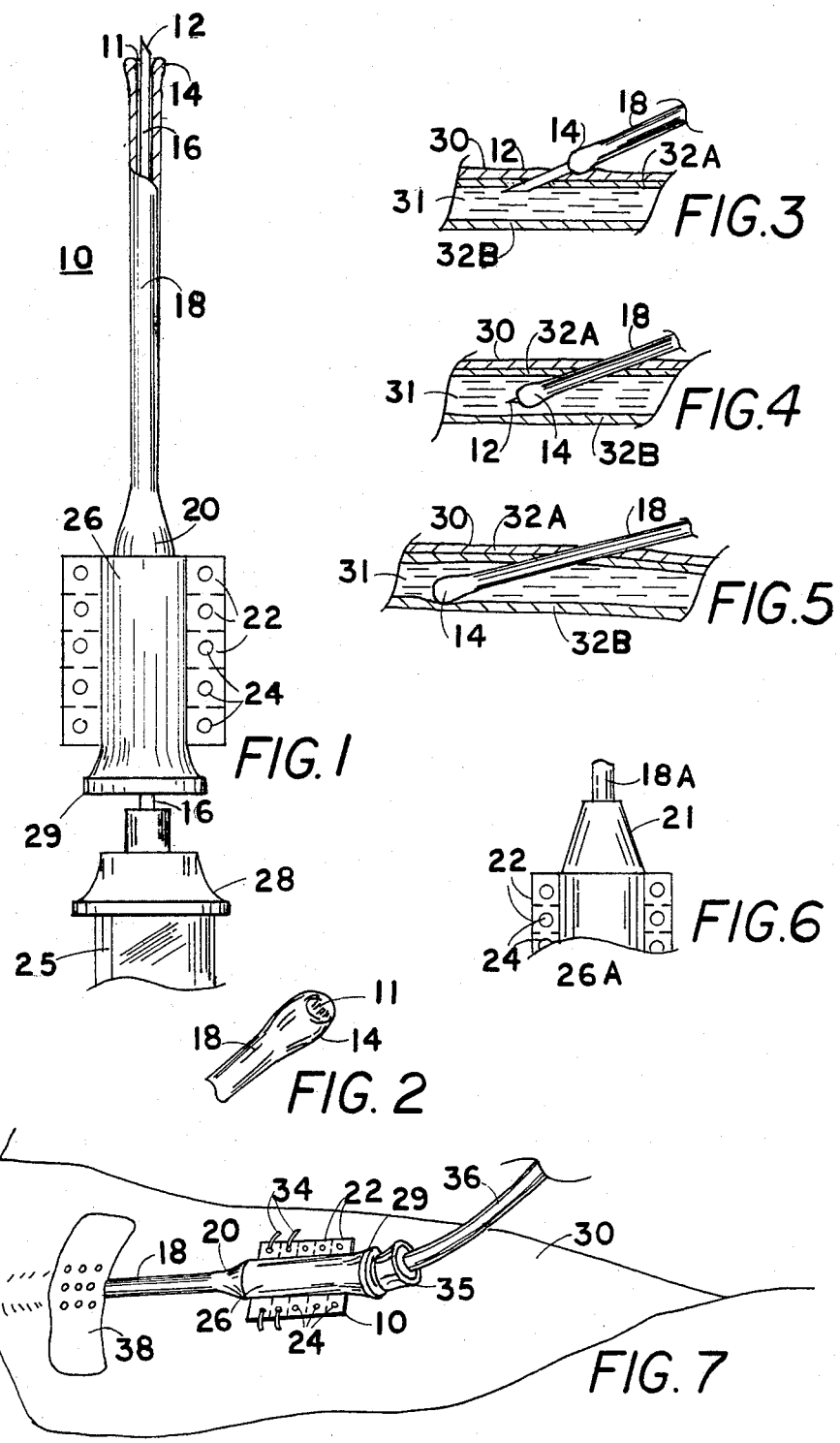

NON-TRAUMATIC BULBOUS CATHETER

BACKGROUND OF THE INVENTION

1. Technical Field

The present invention relates to devices for puncturing blood vessels for the purposes of injecting or extracting fluids, and in particular to intravenous catheters which are resistant to breakage and laceration of the blood vessel and infiltration of the cannulation site.

2. Background Art

A primary problem in penetrating human blood vessels is that the sharp point required to penetrate the flesh and vessel walls cleanly continues to penetrate the flesh and blood vessel walls after it is in place due to various movements and pressures causing further penetration and various lateral movements of the cannula within the patient's body. Serious lacerations and infiltration cause swelling and pain and often delay the healing process after removal of the catheter. Often the catheter must be relocated a number of times causing more damaged sites on the patient's body and wasting the time of the medical staff.

Another problem is the tendency for smooth catheters to slip out of the blood vessel because of the smooth shaft of the typical cannula causing further damage, loss of intravenous fluid and wasting further medical staff time in reinserting the catheter.

Many cannulae, because of the slender delicate shape necessary for blood vessel penetration, are prone either to kink or break off at the hub to which the cannula is secured.

Prior art catheters generally only provide a single perforated tab on each side of the hub for securing the catheter to the patient by suturing. Often the tabs are in a poor location or orientation for properly securing the catheter.

DISCLOSURE OF THE INVENTION

A rounded bulbous tip on the distal end of the cannula in the present invention resolves a number of problems found in the prior art catheters. After the sharply pointed needle inserted within the cannula pierces the blood vessel wall, the sharp needle is removed leaving only the bulbous cannula tip within the vessel thereby greatly decreasing the likelihood of the cannula to lacerate with resultant trauma, coagulation and infiltration.

Because the bulbous tip of the cannula is larger in diameter than the cannula shaft, after slipping through the freshly made hole punctured by the sharp needle insert, the vessel wall closes around the cannula shaft and the larger tip within the vessel is not easily withdrawn by accident because the tendency is for the tip to stay within the vessel wall. When it is necessary to withdraw the cannula after use, the tip may be withdrawn by pulling on the hub to withdraw the cannula. Upon removal of the cannula, the smooth outward flare of the bulbous tip gently expands the vessel wall opening without tearing.

A broad base at the proximal end of the cannula where it connects to the hub provides a strong support for the cannula and thereby reduces the likelihood of breakage and kinking which normally occur at the connection point.

Providing a number of break-away perforated tabs on each of two lateral sides of the hub permits a secure bonding of the catheter to the skin of the patient by suturing through a single close contacting tab to the skin surface or through multiple tabs, and permits the remaining non-sutured tabs to be broken away and discarded.

BRIEF DESCRIPTION OF THE DRAWINGS

These and other details and advantages of our invention will be described in connection with the accompanying drawings, which are furnished only by way of illustration and not in limitation of the invention, and in which drawings:

FIG. 1 is a side elevational view of the intravenous catheter in partial section showing the needle passing therethrough;

FIG. 2 is an enlarged partial perspective view of the bulbous distal end of the cannula;

FIG. 3 is a sectional elevation view through the skin of the patient showing the needle penetration of the blood vessel;

FIG. 4 is a sectional elevation view through the skin of the patient showing the insertion of the cannula into the blood vessel with the needle partially withdrawn;

FIG. 5 is a sectional elevation view through the skin of the patient showing the cannula substantially inserted within the blood vessel with the needle completely withdrawn; FIG. 6 is a partial side elevational view showing an alternate embodiment of the hub with a tapered hub extension rigidly connected to the cannula;

FIG. 7 is a perspective view of a portion of the arm of a patient with the intravenous catheter inserted therein and secured by suturing.

BEST MODE FOR CARRYING OUT THE INVENTION

In FIG. 1 the intravenous catheter 10 comprises an elongated hollow cylindrical cannula 18 of any suitable sterilizable material having a uniform hollow interior 11 which admits a needle 16 having a beveled or tapered sharp point 12 inserted and retracted by an enlarged handle portion 28 and extending viewing chamber 25. When the needle is withdrawn fluids, such as an intravenous solution may flow through the cannula into the blood stream of the patient, or blood withdrawn.

At its distal end, the cannula is provided with a smooth bulbous tip 14 larger in external diameter than the cannula shaft and equal in internal diameter to the cannula hollow. At its proximal end, the cannula 18 is provided with a broad base 20 formed by a flaring outwardly of the cannula at the connecting point to the hub 26 which is rigidly secured to the cannula.

The hub 26 is provided on each of two lateral sides with a series of break-away tabs 22 each provided with a central opening 24 or perforation therethrough for receiving sutures to secure the catheter to the skin of the patient.

In FIG. 2 the bulbous tip 14 of the cannula 18 flares outwardly from the exterior of the cannula shaft and then curves over evenly into the interior hollow 11 of the cannula.

In FIG. 3 the sharp needle point 12 pierces the skin 30 and outer blood vessel wall 32A and the needle point is then extracted as the cannula bulbous end 14 is inserted within the blood vessel 31, as shown in FIG. 4. In FIG. 5 the cannula is substantially inserted within the blood vessel and the sharp needle point completely withdrawn so that the bulbous end of the cannula will not penetrate the inner blood vessel wall 32B under normal conditions despite movement by the patient and pressure applied to the catheter. Further it can be seen that the bulbous end 14 of the cannula is less likely to slip out of the blood vessel than smooth-shafted cannulae.

In FIG. 6 an alternate embodiment of the hub 26A provides a broad based 21 for the cannula 18A by an extension of the hub tapering over a portion of the proximal end of the cannula.

In FIG. 7 the intravenous catheter 10 is sutured 34 through openings 24 in tabs 22 to the skin 30 of the patient to secure the hub 26 while the cannula 18 in within the blood vessel of the patient through a skin opening covered by a bandage 38. A tube 36 connects the hub 26 of the catheter to a source of intravenous fluid fed through the invention into the patient's blood stream.

Although the needle must be made of sharply pointed steel, the cannula and hub may be fabricated of steel or plastic, with a plastic hub and break-away tabs preferred.

When applied to the patient the bulbous tipped intravenous catheter stays in place more readily within the blood vessel, causes significantly less damage and is less likely to break than conventional intravenous catheters. In addition, multiple tabs enable more secure and convenient suture connections with optional choices of suture placement and multiple sutures possible on each side.

It is understood that the preceding description is given merely my way of illustration and not in limitation of the invention and that various modifications may be made thereto without departing from the spirit of the invention as claimed.

We claim:

1. An improved intravenous catheter which is resistant to breaking, lacerating and infiltration and which causes secure convenient suturing attachment, wherein the intravenous catheter comprises:

an elongated cylindrical cannula having a smooth external annular surface and a hollow interior to admit a needle and fluids therethrough, which cannula, at a distal end, comprises a bulbous smooth-surfaced tip flaring externally from the smooth annular surface into a uniformly enlarged external diameter and curving smoothly to form an annular rim which curves smoothly into the hollow interior and a central opening equal in diameter to the hollow cannula interior, and which cannula, at a proximal end, comprises a broad base of greater diameter than the cannula, and extending beyond the broad base and rigidly secured to the broad base and cannula a hollow cylindrical hub wherein said hub comprises a series of break away tabs on each of two opposing sides of the hub, wherein each tab is provided with a central opening through the tab, which opening admits sutures for securing the intravenous catheter to the skin of the patent;

an elongated cylindrical needle sufficiently narrow in external diameter to fit within the cannula and, at a distal end, the needle comprises a sharp angled point for piercing skin and blood vessels of the patient;

which needle is inserted through the cannula tip for piercing through into the blood vessel, wherein the needle is removed after insertion into the blood vessel to permit fluid to flow through the cannula between an external vessel and the interior of the blood vessel.

2. The invention of claim 1 wherein the broad base comprises a flared proximal end of the cannula where the cannula forms a rigid connection with the hub.

3. The invention of claim 1 wherein the intravenous catheter is secured by suture means through at least one of the tabs on each side of the hub and the remaining tabs are broken away.

4. The invention of claim 1 wherein the broad base comprises a frusto-conical extension of the hub along a portion of the proximal end of the cannula.

* * * * *